(12) United States Patent
Park et al.

(10) Patent No.: US 10,555,609 B2
(45) Date of Patent: Feb. 11, 2020

(54) PRESSURE-SENSING CHAIR, INCLUDING FIRST ELASTIC BODY HAVING LOWER ELASTIC MODULUS THAN SECOND ELASTIC BODIES ARRANGED THEREIN

(71) Applicant: LG INNOTEK CO., LTD., Seoul (KR)

(72) Inventors: Yong Hwa Park, Seoul (KR); Bi Yi Kim, Seoul (KR); Jeong Han Kim, Seoul (KR); Hyun Gyu Park, Seoul (KR); Won Keun Cho, Seoul (KR); Hyun Jin Jo, Seoul (KR); In Hee Cho, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 25 days.

(21) Appl. No.: 15/763,630

(22) PCT Filed: Oct. 6, 2016

(86) PCT No.: PCT/KR2016/011208
§ 371 (c)(1),
(2) Date: Mar. 27, 2018

(87) PCT Pub. No.: WO2017/061799
PCT Pub. Date: Apr. 13, 2017

(65) Prior Publication Data
US 2018/0271285 A1  Sep. 27, 2018

(30) Foreign Application Priority Data

Oct. 6, 2015 (KR) .................. 10-2015-0140356
Nov. 9, 2015 (KR) .................. 10-2015-0156814

(51) Int. Cl.
*G01L 1/18* (2006.01)
*A47C 7/02* (2006.01)
(Continued)

(52) U.S. Cl.
CPC .............. *A47C 1/00* (2013.01); *A47C 7/02* (2013.01); *A47C 7/62* (2013.01); *A47C 31/126* (2013.01);
(Continued)

(58) Field of Classification Search
CPC ....... G01L 1/205; A47C 7/021; A47C 7/0213; A47C 7/027; A47C 7/18; A47C 7/185;
(Continued)

(56) References Cited

U.S. PATENT DOCUMENTS 4,429,427 A * 2/1984 Sklar .................. A47C 27/20
5/654.1
5,523,040 A * 6/1996 Krouskop ............ A47C 23/002
264/163
(Continued)

FOREIGN PATENT DOCUMENTS

JP    S62-250390    10/1987
JP    2002-059769    2/2002
(Continued)

OTHER PUBLICATIONS

International Search Report (with English Translation) and Written Opinion dated Jan. 9, 2017 issued in Application No. PCT/KR2016/011208.

*Primary Examiner* — Lisa M Caputo
*Assistant Examiner* — Tran M. Tran
(74) *Attorney, Agent, or Firm* — KED & Associates, LLP

(57) ABSTRACT

A pressure-sensing chair according to one embodiment of the present invention comprises: a first electrode having a first conductive region formed in a first direction; a second electrode having a second conductive region formed in a second direction; a sensing sheet including an intermediate layer arranged between the first electrode and the second electrode; a first elastic body arranged on the sensing sheet
(Continued)

and having a first elastic modulus; and a plurality of second elastic bodies arranged in the first elastic body and having a second elastic modulus, which is greater than the first elastic modulus.

13 Claims, 9 Drawing Sheets

(51) Int. Cl.
  *A47C 1/00*    (2006.01)
  *A47C 31/12*   (2006.01)
  *G01L 1/14*    (2006.01)
  *A47C 7/62*    (2006.01)
  *A61B 5/00*    (2006.01)
  *A61B 5/11*    (2006.01)

(52) U.S. Cl.
  CPC .............. *A61B 5/6891* (2013.01); *G01L 1/14* (2013.01); *G01L 1/146* (2013.01); *G01L 1/18* (2013.01); *A61B 5/002* (2013.01); *A61B 5/1116* (2013.01); *A61B 5/746* (2013.01); *A61B 2562/0247* (2013.01); *A61B 2562/166* (2013.01)

(58) Field of Classification Search
  CPC .. A47C 7/20; A47C 7/287; A47C 7/35; A47C 27/0456; A47C 27/06; A47C 27/065; A47C 27/144; A47C 27/148; A47C 27/16
  See application file for complete search history.

(56) References Cited

U.S. PATENT DOCUMENTS

| | | | | |
|---|---|---|---|---|
| 6,092,249 A * | 7/2000 | Kamen | ................... | A47C 4/54 5/653 |
| 6,155,120 A * | 12/2000 | Taylor | ................ | A61B 5/1036 73/862.046 |
| 6,250,719 B1 * | 6/2001 | Gebhardt | ............... | A47C 7/021 297/219.1 |
| 6,378,948 B1 * | 4/2002 | Macher | .................. | A47C 7/425 297/180.12 |
| 6,687,933 B2 * | 2/2004 | Habboub | ............... | B60N 2/242 297/452.42 |
| 6,704,962 B2 * | 3/2004 | Choi | ..................... | A47C 27/15 5/655.9 |
| 7,077,009 B2 * | 7/2006 | Lokhorst | ................ | G01L 1/205 73/706 |
| 7,159,471 B2 * | 1/2007 | Fortune | .................... | G01G 7/06 177/210 C |
| 7,161,084 B2 * | 1/2007 | Sandbach | ............... | G06F 3/023 174/117 M |
| 7,428,764 B2 * | 9/2008 | Clark | .................... | A47C 27/20 5/655.9 |
| 7,644,461 B2 * | 1/2010 | Lee | ........................ | A47C 27/04 5/655.8 |
| 7,980,144 B2 * | 7/2011 | Chang | .................... | G01L 1/205 73/760 |
| 8,451,013 B1 * | 5/2013 | Hsiao | .................. | G01M 5/0083 324/600 |
| 8,628,067 B2 * | 1/2014 | Pearce | ................. | A47C 27/144 267/142 |
| 8,672,842 B2 * | 3/2014 | Kenalty | ............... | A61B 5/0015 324/691 |
| 8,820,173 B2 * | 9/2014 | Clark | .................... | G01L 1/205 73/768 |
| 8,904,876 B2 * | 12/2014 | Taylor | ...................... | G01L 1/18 361/283.4 |
| 8,966,997 B2 * | 3/2015 | Taylor | ...................... | B32B 5/26 73/862.041 |
| 8,997,588 B2 * | 4/2015 | Taylor | ...................... | G01L 1/00 73/862.041 |
| 9,198,523 B2 * | 12/2015 | Cassaday | ............... | A47C 1/022 |
| 9,411,457 B2 * | 8/2016 | Perlin | ..................... | G06F 3/005 |
| 9,448,127 B2 * | 9/2016 | Cannard | .................. | G01L 1/18 |
| 9,510,690 B2 * | 12/2016 | Rawls-Meehan | ........ | A47C 7/14 |
| 9,630,525 B2 * | 4/2017 | Nakazaki | ............... | B60N 2/002 |
| 9,642,470 B2 * | 5/2017 | Taylor | ..................... | G01L 1/18 |
| 9,645,021 B2 * | 5/2017 | Miura | ....................... | G01L 1/22 |
| 9,671,297 B2 * | 6/2017 | Sibbett | ................... | B25J 19/02 |
| 2013/0167301 A1 * | 7/2013 | Shih | ..................... | A47C 27/081 5/713 |
| 2018/0228420 A1 * | 8/2018 | Kim | ........................ | A61B 5/18 |

FOREIGN PATENT DOCUMENTS

| | | |
|---|---|---|
| JP | 2002-228516 | 8/2002 |
| JP | 2013-111423 | 6/2013 |
| JP | 2014-119306 | 6/2014 |

* cited by examiner

US 10,555,609 B2

PRESSURE-SENSING CHAIR, INCLUDING FIRST ELASTIC BODY HAVING LOWER ELASTIC MODULUS THAN SECOND ELASTIC BODIES ARRANGED THEREIN

CROSS-REFERENCE TO RELATED PATENT APPLICATIONS

This application is a U.S. National Stage Application under 35 U.S.C. § 371 of PCT Application No. PCT/KR2016/011208, filed Oct. 6, 2016, which claims priority to Korean Patent Application No. 10-2015-0140356, filed Oct. 6, 2015, Korean Patent Application No. 10-2015-0156814, filed Nov. 9, 2015, and whose entire disclosures are hereby incorporated by reference.

TECHNICAL FIELD

The present invention relates to a pressure-sensing chair, and more particularly, to a pressure-sensing chair having a pressure sensing sensor included inside a seat of the pressure-sensing chair.

BACKGROUND ART

Recently, with a rapid development of electronic technology and information and communication technology, a health care field is rapidly developing. That is, a health management system capable of using biometric data to measure a body condition of a person is required, and specifically, techniques for acquiring biometric data utilizing chairs mainly used in daily life are being developed.

However, a common chair for acquiring biometric data requires a plurality of independent sensors so as to measure a large area, and a space for connecting modules configured to drive the plurality of independent sensors is additionally required. Further, the plurality of independent sensors have no flexibility and elasticity such that there is a difficulty in application to a chair having multiple curved surfaces.

Technical Problem

It is an objective of the present invention to provide a pressure-sensing chair capable of sensing a pressure and a position according to an applied weight.

Technical Solution

According to an aspect of the present invention, there is provided a pressure-sensing chair including a sensing sheet including a first electrode having a first conductive region formed in a first direction, a second electrode having a second conductive region formed in a second direction, and an intermediate layer disposed between the first electrode and the second electrode, a first elastic body disposed on the sensing sheet and having a first elastic modulus, and a plurality of second elastic bodies arranged in the first elastic body and having a second elastic modulus higher than the first elastic modulus.

The plurality of second elastic bodies may extend in a direction from an upper portion of the first elastic body toward the sensing sheet.

Each of the plurality of second elastic bodies may include a first head unit, a second head unit, and an extension unit connecting the first head unit and the second head unit.

The first head unit and the second head unit may be arranged to correspond to a sensing region in which the first conductive region and the second conductive region intersect each other.

A width of each of the first head unit and the second head unit may be greater than that of the extension unit.

Each of the first conductive region and the second conductive region may include a conductive fiber.

The conductive fiber may include a metal wire or a fiber having a surface coated with a metal film.

The intermediate layer may include a fiber base material and a conductive composite dispersed within the fiber base material.

The pressure-sensing may further include a controller connected to the sensing sheet and configured to generate a control signal according to piezoresistance or capacitance between the first electrode and the second electrode.

The pressure-sensing may further include a communication part configured to transmit the signal generated by the controller.

The pressure-sensing chair may further include a support plate disposed below the sensing sheet and configured to support the sensing sheet.

The sensing sheet may further include a first adhesive layer disposed between the first electrode and the intermediate layer, and a second adhesive layer disposed between the intermediate layer and the second electrode.

The intermediate layer may include an elastic body and a conductive composite dispersed within the elastic body.

The pressure-sensing chair may further include a first connector configured to transmit an electrical signal generated from the first electrode, and a second connector configured to transmit an electrical signal generated from the second electrode.

The intermediate layer may include a first hole formed from a region in contact with a first sheet to a side surface of the intermediate layer and a second hole formed from a region in contact with a second sheet to the side surface of the intermediate layer, the first connector may pass through the first hole, and the second connector may pass through the second hole.

The pressure-sensing chair may further include a controller connected to the first connector and the second connector and configured to process electrical signals generated from the first sheet and the second sheet and generate a control signal according to a processed result, and a communication part configured to transmit the control signal.

Advantageous Effects

In accordance with a pressure sensing device according to the embodiment of the present invention, a pressure can be accurately sensed according to an applied weight and a pressure distribution can also be accurately sensed. Further, in accordance with a pressure sensing device according to the embodiment of the present invention, a large area can be made. Furthermore, in accordance with a pressure sensing device according to the embodiment of the present invention, durability and sensing performance can be improved.

MODES OF THE INVENTION

Figure 1:
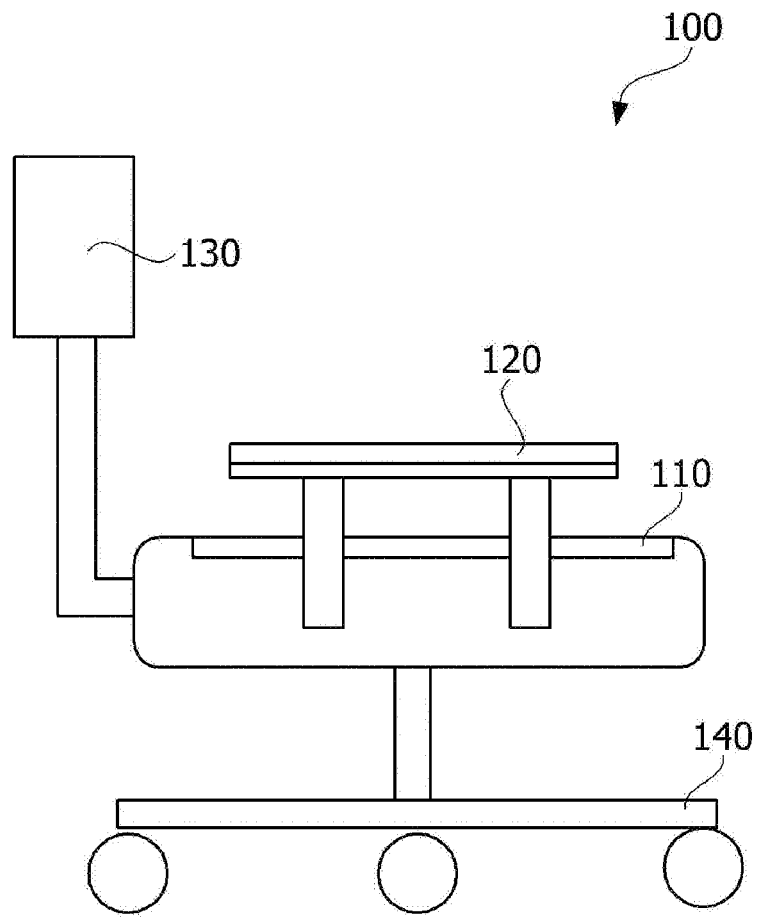
FIG. 1 is a side view of a pressure-sensing chair according to one embodiment of the present invention.

The present invention may be modified into various forms and may have a variety of embodiments, and, therefore, specific embodiments will be illustrated in the drawings and described. The embodiments, however, are not to be taken in a sense which limits the present invention to the specific embodiments, and should be construed to include modifications, equivalents, or substituents within the spirit and technical scope of the present invention.

Also, the terms including ordinal numbers such as first, second, and the like used herein may be used to describe various components, but the various components are not limited by the terms. The terms are used only for the purpose of distinguishing one component from another component. For example, without departing from the scope of the present invention, a second component may be referred to as a first component, and similarly, a first component may also be referred to as a second component. The term "and/or" includes a combination of a plurality of related listed items or any one item of the plurality of related listed items.

When a component is referred to as being "connected," or "coupled" to other component, it may be directly connected or coupled to the other component, but it should be understood that another component may exist between the component and the other component. Contrarily, when a component is referred to as being "directly connected," or "directly coupled" to other component, it should be understood that another component may be absent between the component and the other component.

The terms used herein are employed to describe only specific embodiments and are not intended to limit the present invention. Unless the context clearly dictates otherwise, the singular form includes the plural form. It should be understood that the terms "comprise," "include," and "have" specify the presence of stated herein features, numbers, steps, operations, components, elements, or combinations thereof, but do not preclude the presence or possibility of adding one or more other features, numbers, steps, operations, components, elements, or combinations thereof.

Unless otherwise defined, all terms including technical or scientific terms used herein have the same meaning as commonly understood by those skilled in the art to which the present invention pertains. General terms that are defined in a dictionary shall be construed as having meanings that are consistent in the context of the relevant art and are not to be interpreted as having an idealistic or excessively formalistic meaning unless clearly defined in the present application.

Hereinafter, embodiments of the present disclosure will be described in detail with reference to the drawings, the same reference numerals are given to the same or corresponding components regardless of reference numerals, and a repetitive description thereof will be omitted.

Figure 2:
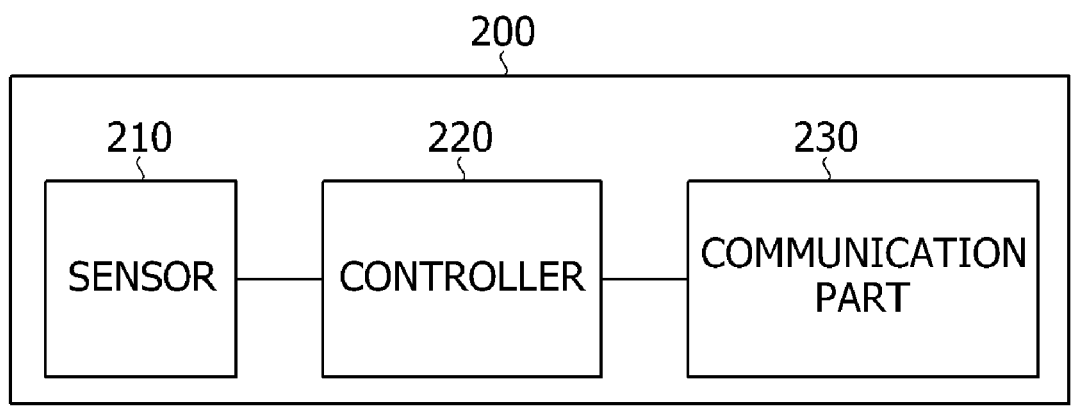
FIG. 2 is a block diagram of a pressure sensing device included inside the pressure-sensing chair according to one embodiment of the present invention.

FIG. 1 is a side view of a pressure-sensing chair according to one embodiment of the present invention, and FIG. 2 is a block diagram of a pressure sensing device included inside the pressure-sensing chair according to one embodiment of the present invention.

Referring to FIGS. 1 and 2, a pressure-sensing chair 100 includes a seat 110, an armrest 120, a backrest 130, and a leg 140. When a person sits on the seat 110, a pressure sensing device 200 included inside the pressure-sensing chair 100 may sense whether the person is sitting and measure a relative pressure distribution caused by the sitting of the person. The pressure sensing device 200 may detect a weight, a sitting posture, and the like according to the measured pressure distribution.

The pressure sensing device 200 may include a sensor 210, a controller 220, and a communication part 230. The sensor 210 may sense whether the person is sitting on the seat 110 and the relative pressure distribution due to the sitting of the person. The sensor 210 may be implemented to be included inside the seat 110. The controller 220 is connected to the sensor 210 and processes a signal sensed by the sensor 210. For example, the controller 220 may control turning the device on or off using a processing result of the signal sensed by the sensor 210. Alternatively, the controller 220 may generate an alarm signal or the like for a posture correction using the result of processing the signal sensed by the sensor 210. Further, the communication part 230 transmits the signal processed by the controller 220 to an external device. The controller 220 and the communication part 230 may be included inside the armrest 120, the backrest 130, and the leg 140.

Figure 3:
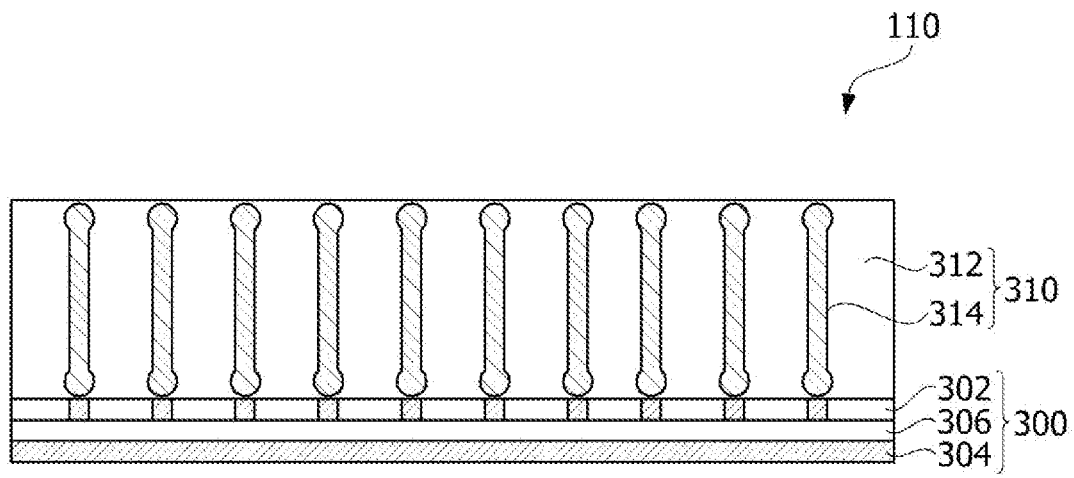
FIG. 3 is a cross-sectional view of a seat including a sensor therein according to one embodiment of the present invention.
Figure 4:
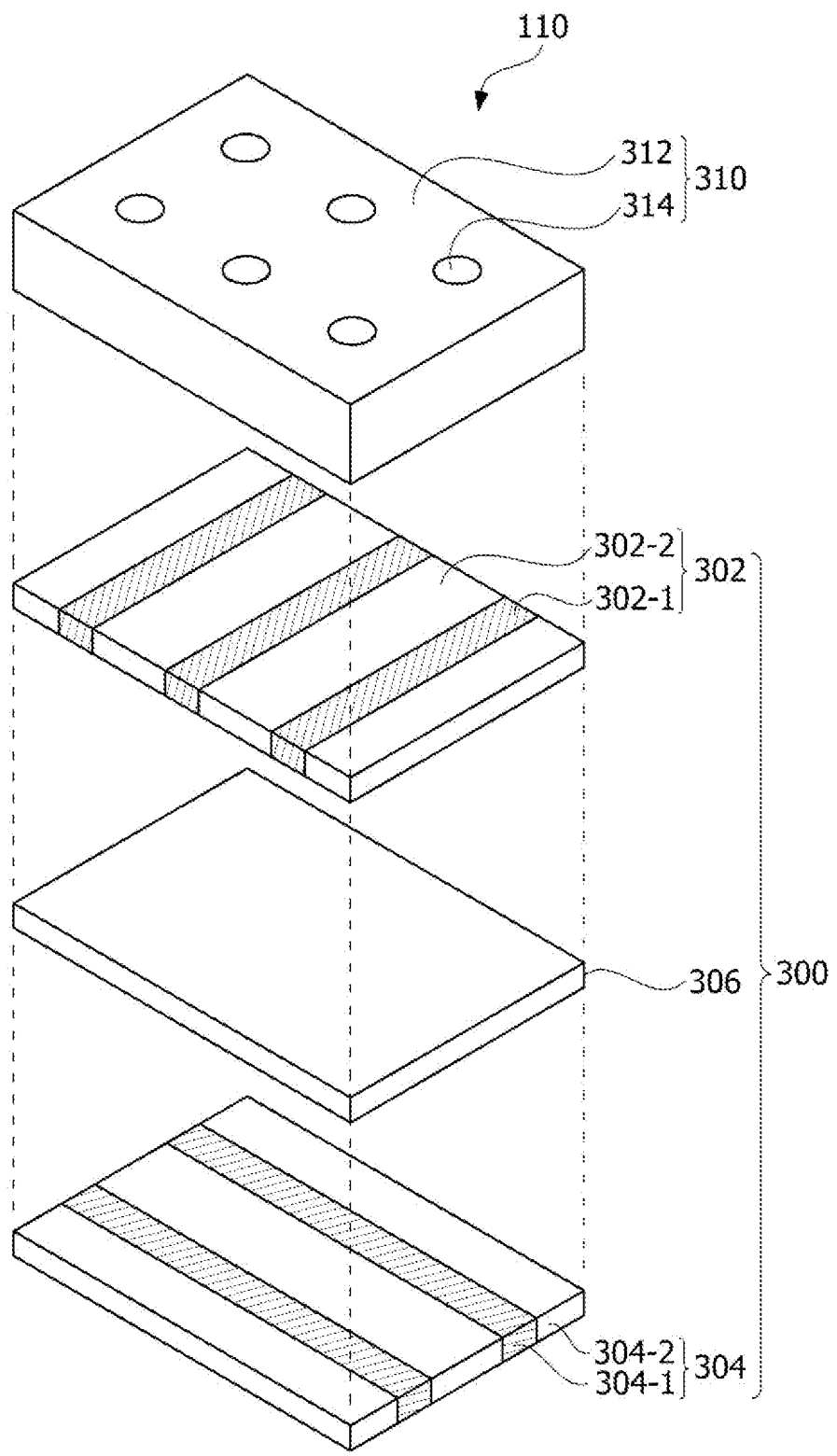
FIG. 4 is an exploded view of the seat including the sensor therein according to the embodiment of the present invention.

FIG. 3 is a cross-sectional view of a seat including a sensor therein according to one embodiment of the present invention, and FIG. 4 is an exploded view of the seat including the sensor therein according to the embodiment of the present invention.

Referring to FIGS. 3 to 4, the seat 110 includes a sensing sheet 300 and a cushion 310 arranged on the sensing sheet 300. Here, the sensing sheet 300 may correspond to the sensor 210 of FIG. 2.

The sensing sheet 300 includes a first electrode 302, a second electrode 304, and an intermediate layer 306 arranged between the first electrode 302 and the second electrode 304. Although not shown in the drawings, the sensing sheet 300 may be enclosed by a cover.

At this point, each of the first electrode 302 and the second electrode 304 may be formed of a fabric containing conductive fibers. Further, the first electrode 302 may include a first conductive region 302-1 formed in a first direction, and the second electrode 304 may include a second conductive region 304-1 formed in a second direction that differs from the first direction.

Furthermore, the intermediate layer 306 may have elasticity, and resistance of the intermediate layer 306 may be higher than that of each of the first electrode 302 and the second electrode 304. At this point, the intermediate layer 306 may also include a fiber base material.

Thus, when each of the first electrode 302 and the second electrode 304 are made of a fabric and the intermediate layer 306 includes a fiber base material, the sensing sheet 300 may be flexible enough to reduce a damage risk thereof and may be implemented in the form of multiple curved surfaces without limitation on a bent radius. Accordingly, it may be widely applied to life appliances, wearable appliances, or the like.

Further, when the first electrode 302 and the second electrode 304 include conductive regions formed in different directions, coordinates regarding an intersecting position between the first conductive region 302-1 and the second conductive region 304-1 may be recognized such that a pressurized position may be accurately sensed. Consequently, a plurality of sensor nodes may be included inside a single sensing sheet 300, and scanning for a large area may be possible.

Further, when the intermediate layer 306 has elasticity, a thickness of the intermediate layer 306 is decreased at a pressurized position. When resistance of the intermediate layer 306 is higher than that of each of the first electrode 302 and the second electrode 304, e.g., the resistance of the intermediate layer 306 is at least 10 times higher, preferably at least 100 times higher, and more preferably at least 1000 times higher than resistance of each of the first electrode 302 and the second electrode 304, the intermediate layer 306 serves to perform an insulation function in a steady state. However, when a pressure is applied on the sensing sheet 300, the thickness of the intermediate layer 306 is decreased and thus resistance or a dielectric constant is varied such that piezoresistance or capacitance may be easily and reliably sensed.

Figure 5:
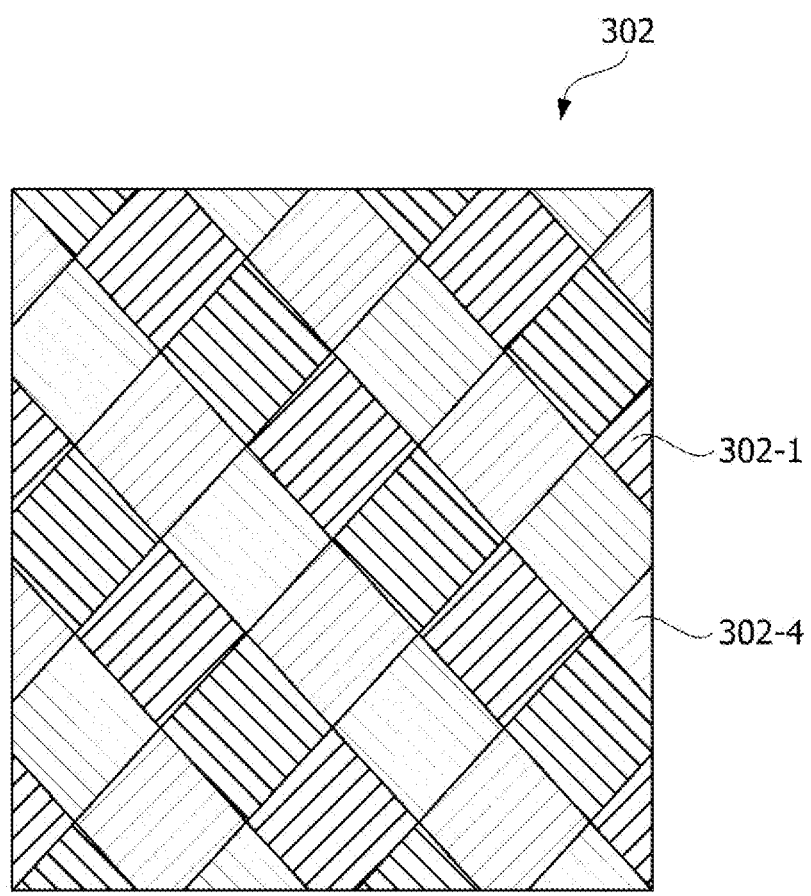
FIG. 5 is an enlarged view of a first electrode according to one embodiment of the present invention.
Figure 6:
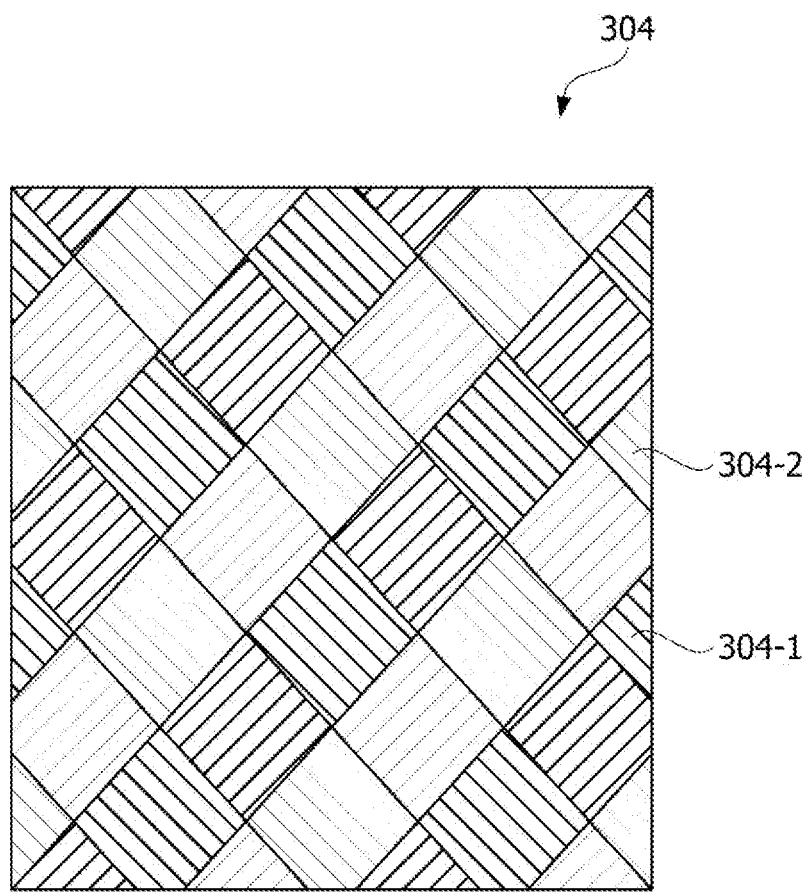
FIG. 6 is an enlarged view of a second electrode according to one embodiment of the present invention.

More specifically, referring to FIGS. 5 to 6, the first conductive region 302 of the first electrode 302 and the second conductive region 304-1 of the second electrode 304 may each be configured with a conductive fiber, and a first non-conductive region 302-2 of the first electrode 302 and a second non-conductive region 304-2 of the second electrode 304 may each be configured with a common fiber. Alternatively, the first conductive region 302-1 of the first electrode 302 and the second conductive region 304-1 of the second electrode 304 may each be formed by alternating common fibers and conductive fibers.

Here, the conductive fiber contained in each of the first conductive region 302-1 and the second conductive region 304-1 may be a metal wire, a common fiber having a surface coated with a metal film, or a common fiber having dispersed metal particles.

At this point, the metal wire may be formed of Cu, Ni, or a stainless steel alloy. For example, the stainless steel alloy may be formed of a martensitic stainless steel alloy, a ferritic stainless steel alloy, an austenitic stainless steel alloy, a duplex stainless steel alloy, a precipitation hardening stainless steel alloy, or the like. When the metal wire is formed of the stainless steel alloy, corrosion resistance of the sensing sheet 300 may be enhanced.

When the conductive fiber contained in each of the first electrode 302 and the second electrode 304 is a common fiber having a surface coated with a metal film, the metal film may be formed by a method in which metal particles are coated on the surface of the common fiber by plating or vapor deposition. At this point, the metal particles may be formed of Cu, Ni, or stainless steel alloys, and a thickness of the metal film may be in the range of 1 μm to 50 μm. When the thickness of the metal film is less than 1 μm, conductivity may be low, causing a loss in signal transmission, and when the thickness of the metal film exceeds 50 μm, the metal film may be easily peeled from the surface of the fiber.

Meanwhile, the intermediate layer 306 contains a fiber base material and a conductive composite. Here, the fiber base material may refer to a random fiber arrangement such as a foam, a non-woven fabric, a nano-web, and the like as well as a fabric made of fibers. At this point, the fiber contained in the fiber base material may be a natural fiber or a synthetic fiber including one selected from the group consisting of polyurethane, nylon, polyethylene terephthalate, and polyester, and a thickness of the fiber base material may be 1 mm or more. Accordingly, fine pores are present in the intermediate layer 306, which has elasticity. When the thickness of the fiber base material is less than 1 mm, it may be difficult to keep an insulation function in a steady state, e.g., in a state in which an external force is not applied, and when the external force is applied, a variation in thickness is small such that a variation in resistance or dielectric constant may be small. Consequently, efficiency in pressure sensing may be lowered.

Meanwhile, the conductive composite contained in the intermediate layer 306 may be coated on the surface of the fiber constituting the fiber base material or be dispersed within the fiber base material.

Thus, resistance of the intermediate layer 306 is 1 kΩ or more in a steady state such that the intermediate layer 306 has an insulation characteristic, but when a physical change occurs around the intermediate layer 306, e.g., when an external force is applied on the intermediate layer 306, a thickness of the intermediate layer 306 is decreased by 0.001 to 0.5 times, the resistance thereof is varied by 100 Ω or more, or the capacitance is varied by 10 pF or more. As described above, when the physical change is applied to the sensing sheet 300, piezoresistance or capacitance is varied.

To this end, the conductive composite may contain a conductive polymer and a conductive powder. The conductive composite may contain 1 to 10 wt % of the fiber base material. When the conductive composite contains more than 10 wt % of the fiber base material, a physical property of the fiber is deteriorated such that a fabric manufacturing may be difficult. At this point, the conductive polymer may contain polyaniline or polypyrrole. Further, the conductive powder may contain one selected from the group consisting of Au, Ag, Cu, Ni, a carbon nano tube (CNT), graphene, and a ceramic filler. Here, the conductive powder may contain 0.1 wt % to 10 wt % of the conductive composite. When the conductive powder contains less than 0.1 wt % of the conductive composite, conductivity is low such that performance is difficult to achieve, and when the conductive powder contains more than 10 wt % of the conductive composite, physical properties of the fiber, such as tensile strength and the like, are deteriorated such that there is a limitation to implementation of the fabric. When the conductive powder contains a ceramic filler, a dielectric constant becomes higher such that a variation in capacitance may be easily sensed. For example, the ceramic filler may be micro carbon coil barium titanate having a diameter of 100 μm or less.

At this point, a diameter of the conductive powder may be in the range of 10 nm to 500 μm, and the conductive powder may be in a spherical, acicular, or plate shape. When the diameter of the conductive powder is less than 10 nm, dispersion into the conductive polymer is difficult and interfacial resistance between particles becomes higher, such that entire resistance of the fiber becomes lower. Further, when the diameter of the conductive powder exceeds 500 μm, the surface of the fiber is not smooth and a frictional force thereof is increased, such that a damage to the fiber may be caused during the fabric manufacturing.

Meanwhile, according to the embodiment of the present invention, the sensing sheet 300 may be disposed below the cushion 310. Accordingly, despite a user repeatedly sitting down and standing up, physical influence on the sensing sheet 300 is minimized such that a damage risk of the sensing sheet 300 is reduced and durability thereof is enhanced.

However, when the sensing sheet 300 is disposed below the cushion 310, sensing sensitivity of the sensing sheet 300 may be lowered. To resolve the lowering of the sensing sensitivity, according to the embodiment of the present invention, the cushion 310 may include a first elastic body 312 having a first elastic modulus and a plurality of second elastic bodies 314 arranged in the first elastic body 312 and having a second elastic modulus higher than the first elastic modulus. At this point, the first elastic body 312 and the plurality of second elastic bodies 314 may each include urethane, a cotton, polyurethane, foam, a sponge made of rubber, or the like. The elastic modulus of each of the plurality of second elastic bodies 314 may be 1.05 to 2 times the elastic modulus of the first elastic body 312. When the user sits on the seat 120, each of the plurality of second elastic bodies 314 having a relatively high elastic modulus is less deformed than the first elastic body 312 having a low elastic modulus. Consequently, weight transfer performance of each of the plurality of second elastic bodies 314 is superior to that of the first elastic body 312.

Figure 7:
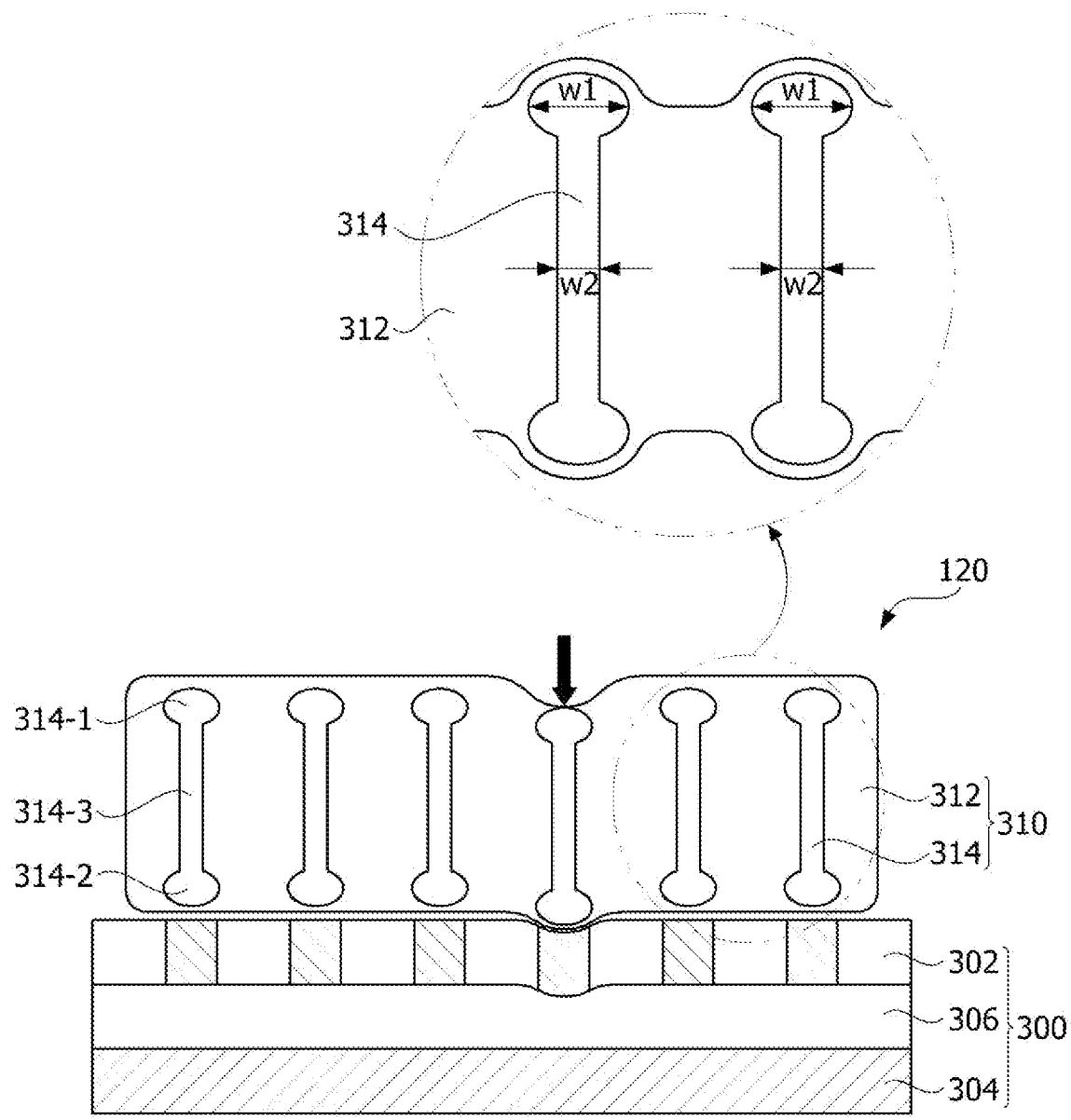
FIG. 7 is a cross-sectional view of a sensing sheet and a cushion according to one embodiment of the present invention.

Specifically, referring to FIG. 7, each of the plurality of second elastic bodies 314 extends to the seat 120, i.e., in a direction from an upper portion of the first elastic body 312 toward the sensing sheet 300, and when the plurality of second elastic bodies 314 are disposed to correspond to sensing regions in which the first conductive region 302-1 of the first electrode 302 and the second conductive region 304-1 of the second electrode 304 intersect each other, a weight applied to an upper portion of the seat 120 is directly transmitted to the sensing regions of the sensing sheet 300 such that sensing performance may be enhanced.

Meanwhile, each of the plurality of second elastic bodies 314 includes a first head unit 314-1, a second head unit 314-2, and an extension unit 314-3 connecting the first head unit 314-1 and the second head unit 314-2. At this point, the first head unit 314-1 may be adjacent to the upper portion of the seat 120, the second head unit 314-2 may be adjacent to the sensing sheet 300, and the first head unit 314-1 and the second head unit 314-2 may be arranged to correspond to the sensing regions in which the first conductive region 302-1 and the second conductive region 304-1 intersect each other. At this point, a width W1 of each of the first head unit 314-1 and the second head unit 314-2 may be greater than a width W2 of the extension unit 314-3. Thus, the plurality of second elastic bodies 314 may be stably brought into contact with the upper portion of the seat 120 and the sensing regions of the sensing sheet 300.

Further, the first head unit 314-1 and the second head unit 314-2 may respectively protrude toward an upper portion and a lower portion of the cushion 310. For example, the first head unit 314-1 and the second head unit 314-2 may have a width in the range of 0.1 mm to 30 cm or less and protrude in height in the range of 0.01 mm to 5 cm or less. As described above, when the first head unit 314-1 and the second head unit 314-2 respectively protrude toward the upper portion and the lower portion of the cushion 310, the first head unit 314-1 and the second head unit 314-2 are brought into closer contact with a part (e.g., a body of the user) pressurizing the cushion 310 and the sensing regions of the sensing sheet 300, such that weight sensing performance may be further enhanced.

Although not shown in the drawing, the seat 110 of the pressure-sensing chair 100 according to the embodiment of the present invention may further include a piezoelectric element. For example, when the user sits on the seat 110 and then stands up, the seat 110 is retracted and then restored. When the above-described occurs repeatedly, electricity may be generated according to a variation in pressure. The electricity generated by the piezoelectric element may be applied to various applications.

Meanwhile, according to the embodiment of the present invention, the first electrode 302 and the second electrode 304, which are included in the sensing sheet 300, may each be bonded to the intermediate layer 306 by an adhesive layer.

Figure 8:
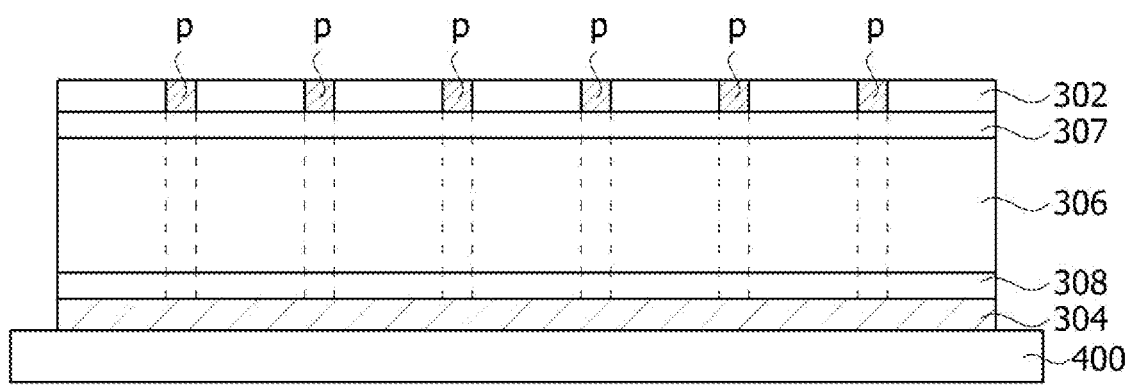
FIG. 8 is a cross-sectional view of a sensing sheet according to one embodiment of the present invention.
Figure 9:
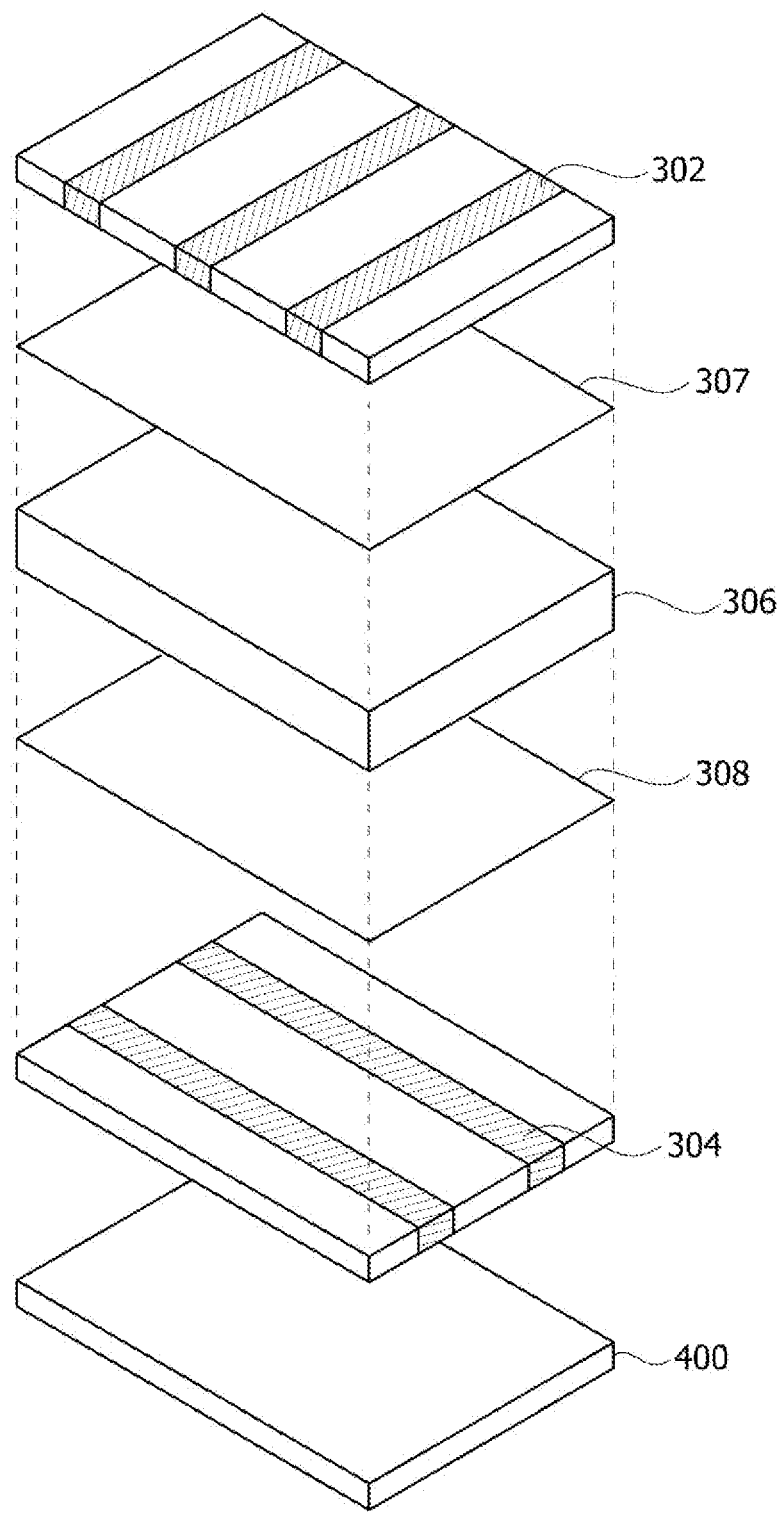
FIG. 9 is an exploded view of the sensing sheet according to one embodiment of the present invention.

FIG. 8 is a cross-sectional view of a sensing sheet according to one embodiment of the present invention, and FIG. 9 is an exploded view of the sensing sheet according to one embodiment of the present invention.

Referring to FIGS. 8 and 9, a sensing sheet 300 may be disposed on a support plate 400 configured to support the sensing sheet 300, and the sensing sheet 300 includes the first electrode 302, the second electrode 304, and the intermediate layer 306 and further includes a first adhesive layer 307 disposed between the first electrode 302 and the intermediate layer 306, and a second adhesive layer 308 disposed between the second electrode 304 and the intermediate layer 306.

Descriptions of the first electrode 302, the second electrode 304, and the intermediate layer 306 overlap with those of FIGS. 3 to 7, and thus overlapping descriptions will be omitted.

Meanwhile, according to the embodiment of the present invention, the first electrode 302 and the second electrode 304, which are included in the sensing sheet 300, may be connected to the controller 220 by passing through the intermediate layer 306.

Figure 10:
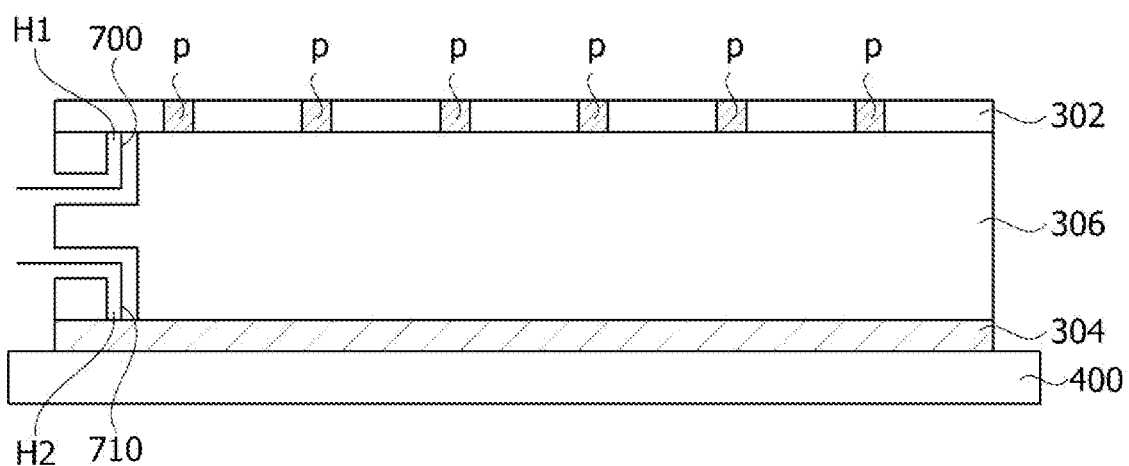
FIG. 10 is a cross-sectional view of a sensing sheet according to another embodiment of the present invention.

FIG. 10 is a cross-sectional view of a sensing sheet according to another embodiment of the present invention.

Referring to FIG. 10, a sensing sheet 300 may be disposed on the support plate 400 configured to support the sensing sheet 300, and the sensing sheet 300 includes the first electrode 302, the second electrode 304, and the intermediate layer 306.

At this point, at least one hole is formed in the intermediate layer 306. For example, the cushion layer 306 may include a first hole H1 formed from a region in contact with the first electrode 302 to a side surface of the intermediate layer 306, and a second hole H2 formed from a region in contact with the second electrode 304 to the side surface of the intermediate layer 306.

Further, a first connector 700 configured to transmit an electrical signal generated from the first electrode 302 passes through the first hole H1, and a second connector 710 configured to transmit an electrical signal generated from the second electrode 304 passes through the second hole H2. Thus, the first connector 700 and the second connector 710 may be connected to the controller 220 and may efficiently transmit the electrical signals generated from the first electrode 302 and the second electrode 304. Here, the first connector 700 and the second connector 710 may be implemented on a flexible printed circuit board (FPCB).

As described above, when the first connector 700 and the second connector 710 pass through the intermediate layer 306 and are connected to the controller 220, there is no concern for the first connector 700 and the second connector 710 from escaping such that durability of the pressure-sensing chair is superior even when the pressure-sensing chair is used for a long period of time.

Although the description has been made with reference to the preferred embodiments of the present invention, it should be understood that various alternations and modifications of the present invention can be devised by those skilled in the art to which the present invention pertains without departing from the spirit and scope of the present invention, which are defined by the appended claims.

DESCRIPTION OF REFERENCE NUMERALS

300: sensing sheet
302: first electrode
304: second electrode
306: intermediate layer
310: cushion
312: first elastic body
314: second elastic body

The invention claimed is:

1. A pressure-sensing chair comprising:
a sensing sheet including a first electrode having a plurality of first conductive regions formed in a first direction and a plurality of first non-conductive regions formed in the first direction, a second electrode having a plurality of second conductive regions formed in a second direction and a plurality of second non-conductive regions formed in the second direction, and an intermediate layer disposed between the first electrode and the second electrode, and the sensing sheet including a plurality of sensing regions corresponding to regions where the plurality of first conductive regions intersect the plurality of second conductive regions; and
a cushion on the sensing sheet, the cushion including:
a first elastic body disposed on the sensing sheet and having a first elastic modulus; and
a plurality of second elastic bodies arranged in the first elastic body and having a second elastic modulus higher than the first elastic modulus, wherein the plurality of second elastic bodies extend in a direction from an upper portion of the first elastic body toward the sensing sheet, wherein each of the plurality of second elastic bodies includes a first head unit adjacent to an upper surface of the cushion, a second head unit adjacent to the sensing sheet, and an extension unit connecting the first head unit and the second head unit, and a width of the first head unit is greater than a width of the extension unit, and a width of the second head unit is greater than the width of the extension unit,
wherein the cushion is disposed on the sensing sheet such that the first electrode is in direct contact with the cushion and each second head unit of the cushion is vertically adjacent to a different one of the sensing regions of the sensing sheet, and the first elastic body of the cushion is provided between each of the second head units of the cushion such that the first elastic body of the cushion is vertically adjacent to each of the plurality of first non-conductive regions.

2. The pressure-sensing chair of claim 1, wherein each of the plurality of first conductive regions and each of the plurality of second conductive regions include a conductive fiber.

3. The pressure-sensing chair of claim 2, wherein the conductive fiber includes a metal wire or a fiber having a surface coated with a metal film.

4. The pressure-sensing chair of claim 2, wherein the intermediate layer includes a fiber base material and a conductive composite dispersed within the fiber base material.

5. The pressure-sensing chair of claim 1, further comprising a controller connected to the sensing sheet and configured to generate a control signal according to piezoresistance or capacitance between the first electrode and the second electrode.

6. The pressure-sensing chair of claim 5, further comprising a communication device configured to transmit the signal generated by the controller.

7. The pressure-sensing chair of claim 1, further comprising a support plate disposed below the sensing sheet and configured to support the sensing sheet.

8. The pressure-sensing chair of claim 1, wherein the sensing sheet further includes a first adhesive layer disposed between the first electrode and the intermediate layer, and a second adhesive layer disposed between the intermediate layer and the second electrode.

9. The pressure-sensing chair of claim 1, wherein the intermediate layer includes an elastic material and a conductive composite dispersed within the elastic body.

10. The pressure-sensing chair of claim 1, further comprising:
a first connector configured to transmit an electrical signal generated from the first electrode; and
a second connector configured to transmit an electrical signal generated from the second electrode.

11. The pressure-sensing chair of claim 10, wherein:
the intermediate layer includes a first hole formed from a region in contact with the first electrode to a side surface of the intermediate layer and a second hole formed from a region in contact with the second electrode to the side surface of the intermediate layer;
the first connector passes through the first hole; and
the second connector passes through the second hole.

12. The pressure-sensing chair of claim 11, further comprising:
a controller connected to the first connector and the second connector, and configured to process electrical signals generated from the first electrode and the second electrode and generate a control signal according to a processed result; and
a communication device configured to transmit the control signal.

13. The pressure-sensing chair of claim 1, wherein the second elastic modulus is 1.05 to 2 times higher than the first elastic modulus.

* * * * *